United States Patent [19]

Lukàc et al.

[11] Patent Number: 4,952,716
[45] Date of Patent: Aug. 28, 1990

[54] ETHYNYLCYCLOHEXENE COMPOUNDS

[75] Inventors: Teodor Lukàc, Aesch, Switzerland; Milan Soukup, Passaic, N.J.

[73] Assignee: Hoffmann-La Roche Inc., Nutley, N.J.

[21] Appl. No.: 164,304

[22] Filed: Mar. 4, 1988

[30] Foreign Application Priority Data

Mar. 27, 1987 [CH] Switzerland .......................... 1191/87

[51] Int. Cl.$^5$ .......................... C07F 7/18; C07C 31/00; C07C 43/00; C07D 309/18
[52] U.S. Cl. .................................... 556/482; 549/421; 568/591; 568/668; 568/824; 568/825
[58] Field of Search ................. 556/482; 568/591, 631, 568/667, 824, 825, 668; 549/421

[56] References Cited

U.S. PATENT DOCUMENTS 4,153,615  5/1979  Saucy .
4,544,770  10/1985 Broger .
4,701,540  10/1987 Lukac et al. .

OTHER PUBLICATIONS

J. Org. Chem. 45, 917 (1980).
Synthesis 459 (1981).
Food Chemistry 5, 15 (1980).
J. Chem. Soc. (c), 404, 1971.
Chem. Abstr. 94, 83655g.
Islamabad J. Sci. 5, 42 (1978).
Pure and Appl. Chem. 51, 535 (1979).

Primary Examiner—John Doll
Assistant Examiner—Stuart L. Hendrickson
Attorney, Agent, or Firm—George M. Gould; John J. Schlager; Paul G. Lunn

[57] ABSTRACT

A process for the manufacture of compounds of the general formula

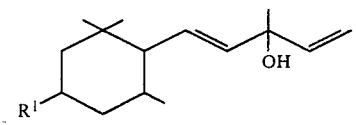

IV wherein $R^1$ signifies hydroxy or an etherified hydroxy group, and of zeaxanthin by converting a compound of the general formula

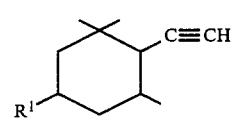

I wherein $R^1$ has the above significance, in an inert organic solvent into the acetylenide and reacting this with methyl vinyl ketone, reducing the alcoholate obtained or the alcohol (obtained after hydrolysis of the alcoholate) of the general formula

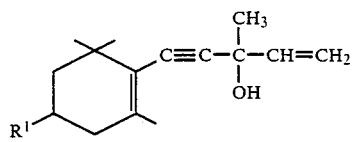

II wherein $R^1$ has the above significance, and subsequently hydrolyzing to give the compound of formula IV and, if desired, converting the compound of formula IV obtained into zeaxanthin.

6 Claims, No Drawings

ETHYNYLCYCLOHEXENE COMPOUNDS

SUMMARY OF THE INVENTION

The present invention is concerned with intermediates in the synthesis of zeaxanthin as well as with ethynylcyclohexene derivatives.

BACKGROUND OF THE INVENTION

Various processes for the manufacture of zeaxanthin starting from isophorone, ketoisophorone or its derivatives have already been described in the literature. However, the known processes have certain disadvantages such as a large number of overall steps or problematic individual steps and give unsatisfactory overall yields.

DETAILED DESCRIPTION OF THE INVENTION

The process in accordance with the invention for the manufacture of zeaxanthin and of zeaxanthin intermediates comprises converting a compound of the general formula

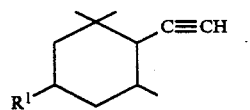
I wherein $R^1$ signifies hydroxy or an etherified hydroxy group,
in an inert organic solvent into the acetylenide and reacting this with methyl vinyl ketone, reducing the alcoholate obtained or the alcohol (obtained after hydrolysis of the alcoholate) of the general formula

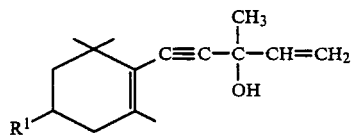
II wherein $R^1$ has the above significance,
in an inert organic solvent with an aluminium hydride of the general formula

III wherein M signifies alkali metal, R represents $C_1$-$C_{10}$-alkoxy or a group of the formula $C_nH_{2n+1}$—O—$C_mH_{2m}$—O—, m and n each individually denote whole numbers of 1 to 7 and x stands for 0, 1, 2 or 3,
and subsequently hydrolyzing to give the compound of the general formula

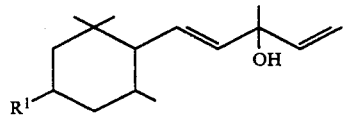
IV wherein $R^1$ has the above significance,
and, if desired, converting the compound of formula IV obtained into zeaxanthin.

In accordance with the present process the manufacture of the compounds of formula IV is effected by the stepwise introduction of the 3-hydroxy-3-methyl-1,4-pentadienyl group via compounds of formula I and reaction with an $\alpha,\beta$-unsaturated ketone to give compounds of formula II or their alcoholates. Surprisingly in this manner a considerable improvement in the overall yield and a simplification of the overall process can be achieved. All steps of this process, including the production of the compounds of formula I, can be carried out readily on an industrial scale. Further, expensive purification operations can be avoided. If, for example, the compound of formula IV is converted into zeaxanthin via a phosphonium salt, then a purification of the compounds of formulae I, II and IV can be dispensed with and only a recrystallization of the phosphonium salt is effected. If desired, the hydroxy compound of formula I can also be purified readily by recrystallization.

The process in accordance with the invention is especially suitable for the manufacture of natural (3R,3′R)-zeaxanthin. The conversion of the compounds of formula I into the compounds of formula IV, including the introduction of etherified hydroxy groups $R^1$, can preferably also be carried out as a one-pot process.

The term "etherified hydroxy group" embraces in the scope of the present invention usual ether protecting groups, for example alkoxy such as methoxy, ethoxy, t-butoxy or isobutoxy, arylalkoxy such as benzyloxy, trialkylsilyloxy such as trimethylsilyloxy or groups of the general formula

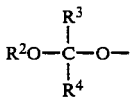
V wherein $R^2$ signifies alkyl and $R^3$ and $R^4$ each independently signify hydrogen or alkyl or $R^2$ and $R^3$ together also signify tetramethylene.

Preferably, in the aforementioned groups alkyl stands for $C_1$-$C_7$-alkyl, alkoxy stands for $C_1$-$C_7$-alkoxy and aryl stands for phenyl. Preferred etherified hydroxy groups are trialkylsilyloxy and the groups of formula V such as trimethylsilyloxy, 1-methoxy-1-methylethoxy, tetrahydropyranyloxy and the like.

The term "alkali metal" embraces lithium, sodium and potassium. The term "halogen" embraces fluorine, chlorine, bromine and iodine, preferably chlorine and bromine. The term "alkyl" embraces especially $C_1$-$C_7$-alkyl such as methyl, ethyl or butyl. The term "aryl" embraces especially carbocyclic groups such as phenyl, tolyl and the like, especially phenyl. The term "acyloxy" denotes usual ester protecting groups such as benzoyloxy and $C_1$-$C_7$-alkanoyloxy, especially acetoxy.

The reaction of a compound of formula I with methyl vinyl ketone to give an alcohol of formula II or its alcoholate can be effected in a manner known per se in an inert organic solvent. Examples of suitable solvents are the ethers and the saturated or aromatic hydrocarbons such as tetrahydrofuran, dioxan, diethyl ether, petroleum ether, hexane, benzene, toluene, xylene and the like. The ethers, especially tetrahydrofuran, are preferred solvents. The reaction can be effected with a compound of formula I in which $R^1$ signifies hydroxy. However, a compound of formula I in which $R^1$ signifies an etherified hydroxy group, especially trialkylsilyloxy or a group of formula V. is preferably used.

The deprotonization of the compounds of formula I can be effected with suitable bases which are customary for the deprotonization of acetylenes, especially with lithium, sodium or magnesium bases. Examples of suitable bases are lithium-organic compounds such as methyllithium, butyllithium or phenyllithium, Grignard reagents such as alkylmagnesium halides and dialkylmagnesium, amides such as lithium amide and sodium amide, hydrides such as lithium hydride and sodium hydride, and the like. Alkyllithium and alkylmagnesium bromide are preferred bases. A slight excess of base based on the compound of formula I, for example about 1.1–1.3 equivalents, is preferably used.

The methyl vinyl ketone is preferably used in excess based on the compound of formula I. At least about 1.3 mol equivalents of methyl vinyl ketone are preferably used. In general, an amount of about 1.4–2.0 mol equivalents especially about 1.5–1.8 mol equivalents, is preferred.

The reaction with methyl vinyl ketone is preferably effected in the presence of an inorganic lithium or cerium salt. In this case, care should be taken that the salt is sufficiently soluble in the solvent which is used. Examples of suitable salts are lithium halides, cerium halides, lithium tetrafluoroborate and the like. Cerium trichloride and especially lithium bromide are preferred. The amount of lithium or cerium salt is not critical and can amount to, for example, about 0.5–2.0 equivalents or less based on the compound of formula I.

The temperature and pressure in the conversion of a compound of formula I to the alcoholate of the compound of formula II are not critical. However, the conversion is generally carried out at atmospheric pressure and room temperature or a lower temperature, for example to about −30° C. A temperature range of about −20° C. to about 0° C. is especially preferred. Corresponding to the preferred bases there is preferably obtained the lithium, sodium or magnesium alcoholate of the compound of formula II.

If desired the alcoholate obtained can be hydrolyzed to the alcohol of formula II. The hydrolysis can be effected according to usual methods for the hydrolysis of alcoholates, for example with water. However, the alcoholate is preferably not hydrolyzed, but is converted directly into the compound of formula IV, as less reducing agent is consumed in this manner.

The compound of formula II or its alcoholate can be reduced in a manner known per se with an aluminium hydride of formula III. In this case the triple bond is, in general, reduced exclusively to the trans double bond. The reduction is conveniently carried out in an inert organic solvent. Examples of suitable solvents are the solvents given above in connection with the reaction of the compounds of formula I, especially the solvents referred to there as being preferred. Preferably, the alcoholate, without isolation can be reduced directly in the same solvent with an aluminium hydride of formula III. The temperature and pressure are not critical As the reduction proceeds rapidly, especially in the case of the alcoholates even at low temperatures, the reduction is preferably carried out at about −50° C. to room temperature, especially at about −20° C. to about 0° C. In the case of the reduction of the alcohol of formula II a higher temperature, for example room temperature, can be of advantage.

Preferred reducing agents of formula III are those in which M signifies lithium or sodium. Further, x preferably stands for 1, 2 or 3, especially for 2. R preferably signifies a group of the formula $C_nH_{2n+1}$—O—$C_mH_{2m}$—O—. m and n each preferably denote a number of 1 to 3. Sodium dihydrido-bis(2-methoxyethoxy)aluminate is an especially preferred reducing agent. The reducing agent can be used in about equivalent amounts or preferably in excess. An amount at least about 1.2 equivalents, for example about 1.28–1.5 equivalents. of reducing agent is preferred. However, a larger excess is not detrimental When the alcohol of formula II is reacted, an appropriately higher amount is preferably used, as the reducing agent is partially consumed for the deprotonization of the alcohol.

The hydrolysis of the intermediately formed aluminium complex can be effected in a manner known per se, for example with water, with organic or inorganic acids such as p-toluenesulphonic acid, dilute sulphuric acid, dilute hydrochloric acid and the like or preferably, with alkalis such as sodium hydroxide solution, or potassium hydroxide solution. If desired, the hydrolysis can be carried out in such a manner that the ether groups which are optionally present are simultaneously hydrolyzed. The conditions under which the protecting groups used here remain or are cleaved off are fundamentally known to the person skilled in the art. However, in general, it can be said that the protecting groups remain under neutral or basic conditions and in some cases also under weakly acidic conditions, while they are cleaved off under acidic, especially under strongly acidic, conditions. The temperature and pressure are not critical However, in general, the hydrolysis is carried out at atmospheric pressure and room temperature or a lower temperature, preferably at about 0° C. to room temperature The compounds of formula IV can be converted into zeaxanthin according to known methods. In accordance with a preferred variant a compound of formula IV is reacted with a hydrogen halide and a triarylphosphine to give the phosphonium salt of the general formula

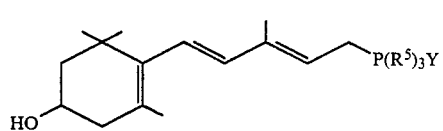

VI wherein $R^5$ signifies aryl and Y signifies halogen, and the phosphonium salt is subsequently condensed with the dialdehyde of the formula

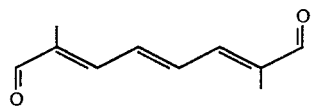

VII to give zeaxanthin. The reaction can be effected according to the methods described in pure and Appl. Chem 51, 535 (1979) and in J. Chem. Soc. C 404 (1971). Ether protecting groups optionally present in formula IV can be cleaved off before or during the formation of the phosphonium salt. The purification is advantageously effected by recrystallization of the phosphonium salt. If desired, the portion of trans compound can be improved by thermal isomerization, e.g. by heating in toluene.

The compounds of formulae I and II and the alcoholates of the compounds of formula II are novel and are also objects of the present invention.

The compounds of formula I can be produced according to the process represented in Scheme I in which $R^1$ has the above significance, $R^6$ denotes an etherified hydroxy group, especially one of the etherified hydroxy groups mentioned earlier, and $R^7$ signifies an acyloxy group, especially acetoxy.

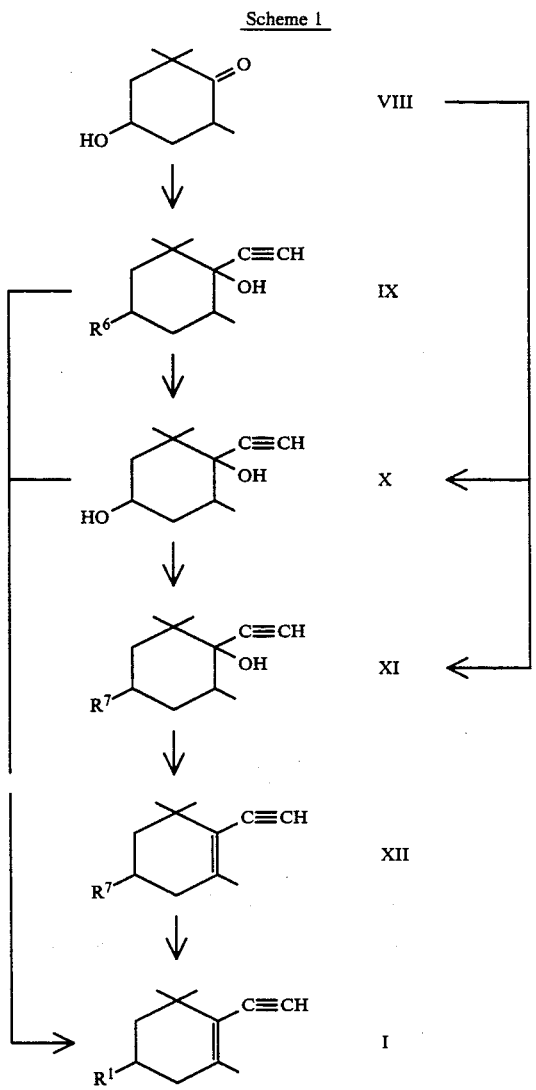

Scheme 1

The production of the compounds of formula I is effected in accordance with Scheme 1 from the compounds of formula VIII via compounds of formulae IX, X or XI, which can be combined in the general formula

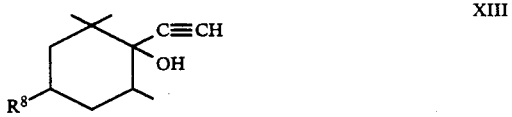

XIII wherein $R^8$ signifies hydroxy, an etherified hydroxy group or an acyloxy group.

The conversion of the compound of formula VIII into a compound of formula IX is effected by etherification of the hydroxy group and subsequent ethynylation at the keto group. Suitable etherification methods such as reaction with an alkyl halide, aralkyl halide, trialkyl- chlorosilane, alkyl 1-alkenyl ether, 3,4-dihydro-2H-pyran and the like are known to the person skilled in the art. The ethynylation can also be effected in a manner known per se, for example with lithium, sodium or calcium acetylide in liquid ammonia or preferably with a lithium acetylide-ammonia complex in an inert organic solvent, e.g. tetrahydrofuran or hexane. The product obtained predominantly has the hydroxy group in the desired cis-position to the vicinal hydrogen atom.

The hydrolysis of the compounds of formula IX to the diol of formula X can be effected in a manner known per se, e.g. with organic or inorganic acids such as pyridinium p-tosylate, p-toluenesulphonic acid, sulphuric acid and the like.

The diol of formula X can also be obtained directly from the compound of formula VIII by ethynylation of the keto group in an analogous to the method described above. However, in this case there is obtained as a rule a cis/trans mixture with respect to the position of the tertiary hydroxy group and the vicinal hydrogen atom.

The acylation of the diol of formula X to give a compound of formula XI can also be carried in a manner known per se, for example with an acyl anhydride or acyl halide, and is effected selectively at the secondary hydroxy group.

The compounds of formula XI can also be obtained directly from the compound of formula VIII by acylation of the hydroxy group and subsequent ethynylation at the keto group. The acylation can be effected in a manner known per se, for example with an acyl anhydride or acyl halide. The ethynylation can also be effected in a manner known per se, for example according to the methods given in the production of the compounds for formula IX. In this case the hydroxy group is also formed predominantly in the cis-position relative to the vicinal hydrogen atom.

The dehydration of the compounds of formulae IX and X, which leads directly to compounds of formula I, and the dehydration of the compounds of formula XI are preferably carried out in the presence of copper sulphate. The reaction is effected by heating to preferably at least about 140° C. and is preferably carried out in an inert solvent having a boiling point of at least about 140° C., for example o-xylene or silicon oil. The copper sulphate can be used in catalytic amounts, preferably in about 1–20 mol % based on the educt.

The compounds of formula XII can be converted in a manner known per se into compounds of formula I by hydrolysis of the ester group $R^7$ and, if desired, etherification of the hydroxy group. The hydrolysis of the ester group $R^7$ is preferably effected with alkalis such as sodium hydroxide solution or potassium hydroxide solution in an alcohol such as methanol or ethanol. Suitable etherification methods such as reaction with an alkyl halide, aralkyl halide, trialkylchlorosilane, alkyl 1-alkenyl ether, 3,4-dihydro-2-H-pyran and the like are well-known to the person skilled in the art.

As a rule, the conversion via compounds of formulae XI and XII gives higher yields than the direct dehydration of the compounds of formulae IX and X and, moreover, permits a simple purification by distillation of the compound of formula XII.

The production of the compounds of formula I is therefore preferably effected by dehydrating a compound of formula XIII in the presence of copper sulphate, hydrolyzing an acyloxy group which may be present and, if desired, etherifying a free hydroxy group. Preferably, the etherification can be effected in situ prior to the further reaction.

The present process enables zeaxanthin to be manufactured in yields of above 70% based on the compound of formula VIII. It is especially suitable for the manufacture of natural (3R,3'R)-zeaxanthin. In this case, (4R,6R)-4-hydroxy-2,2,6-trimethylcyclohexanone is preferably used as the starting material of formula VIII. In this manner there are obtained exclusively compounds of the above formulae which have the optionally protected, secondary hydroxy group in the R-configuration and, in the case of intermediates of formula XIII, the tertiary hydroxy group in the S-configuration and the methyl group in the R-configuration.

The process in accordance with the invention and the production of the starting materials are illustrated in more detail by the following Examples.

EXAMPLE 1

(a) 30 g of (R)-4-ethynyl-3,5,5-trimethyl-3-cyclohexen-1-ol were dissolved in 200 ml of absolute tetrahydrofuran under argon. The solution was treated with 0.5 g of pyridinium p-tosylate, then treated at 20°–24° within 10 minutes with 43.5 ml of isopropenyl methyl ether and stirred at room temperature for a further 1 hour.

(b) The resulting solution of (R)-4-ethynyl-1-(1-methoxy-1-methylethoxy)-3,5,5-trimethyl-3-cyclohexene was treated dropwise at −10° C. to −12° C. within 10 minutes with 140 ml of a 1.56M solution of butyllithium in hexane and stirred at this temperature for a further 10 minutes. The mixture was then treated dropwise at −10° C. within 5 minutes with a solution of 15.6 g of lithium bromide in 150 ml of absolute tetrahydrofuran and stirred for a further 15 minutes. The reaction solution was subsequently treated at −12° C. to −10° C. within about 10 minutes with 22 ml of methyl vinyl ketone and stirred for a further 30 minutes.

(c) Thereafter, the reaction solution [containing the lithium salt of (R)-1-[4-(1-methoxy-1-methylethoxy)-2,6,6-trimethyl-1-cyclohexenyl]-3-methyl-4-penten-1-yn-3-ol] was treated at −12° C. to −8° C. within 5 minutes with 63 ml of a 3.5M solution of sodium dihydrido-bis(2-methoxyethoxy)aluminate in toluene. The resulting suspension was stirred at −10° C. for 10 minutes and at 0° C. for 40 minutes. Thereafter, the suspension was cooled to −5° C., treated firstly within 10 minutes with a mixture of 40 ml of ethanol and 60 ml of hexane and then within 5 minutes with 300 ml of 28 percent sodium hydroxide solution and stirred vigorously at 0°–5° C. for a further 10 minutes. The reaction mixture was subsequently poured into a mixture of 600 ml of 28 percent sodium hydroxide solution and 1200 ml of hexane. The aqueous phase was separated and extracted twice with 800 ml of hexane each time. The organic phases were washed twice with 250 ml of 28 percent sodium hydroxide solution each time dried over sodium sulphate and filtered. The filtrate was evaporated in a rotary evaporator under a water-jet vacuum at 40° C. bath temperature and the oily residue was dried at 60° C. for 4 hours in a high vacuum. There were thus obtained 54.0 g of crude (R)-1-[4-(1-methoxy-1-methylethoxy)-2,6,6-trimethyl-1-cyclohexenyl]-3-methyl-1E,4-pentadien-3-ol as a light yellow oil which can be used further without additional purification.

EXAMPLE 2

(a) 56.6 g of triphenylphosphine were suspended in 175 ml of methanol under argon. The suspension was cooled to 0° C., treated while stirring at 0° C. within 5 minutes with 19 ml of 37 percent hydrochloric acid and stirred at 0° C. for a further 10 minutes. The suspension was subsequently treated dropwise at 0° C. within about 3 hours with a solution of 54.8 g of crude (R)-1-[4-(1-methoxy-1-methylethoxy)-2,6,6-trimethyl-1-cyclohexenyl]-3-methyl-1E,4-pentadien-3-ol (prepared according to Example 1) in 56 ml of methanol. The reaction mixture was stirred at 0° C. for a further 30 minutes and at room temperature for 16 hours, then diluted with 90 ml of water and poured into 200 ml of hexane. The methanolic phase was extracted three times with 200 ml of hexane each time, then treated with 150 ml of water and 7.5 g of active charcoal, stirred at room temperature for 20 minutes and filtered. The filtrate was concentrated to a volume of 250–300 ml (removal of the methanol) in a rotary evaporator under a water-jet vacuum at 40°–45° C. bath temperature and then treated with 250 ml of water and 90 ml of saturated sodium chloride solution. The mixture was extracted three times with 250 ml of methylene chloride each time. The organic phases were washed with 250 ml of water and with 90 ml of saturated sodium chloride solution, dried over sodium sulphate and filtered. The filtrate was evaporated in a rotary evaporator under a water-jet vacuum at 40° C. bath temperature. The yellowish residue (116.5 g) was dissolved in 110 ml of 1,2-dichlorethane under argon at 30°–40° C. The solution was treated at room temperature within 4 hours with 600 ml of ethyl acetate. The suspension obtained was stirred at room temperature overnight, then cooled to 0° C. and stirred at 0° C. for a further 30 minutes. The crystals were filtered off under suction, washed with 300 ml of cold ethyl acetate and with 300 ml of hexane and then dried at 45°–50° C. for 1 hour in a water-jet vacuum and at room temperature overnight in a high vacuum. There were thus obtained 81.97 g of (R)-5-(4-hydroxy-2,6,6-trimethyl-1-cyclohexenyl)-3-methyl-2,4-pentadienyl-triphenylphosphonium chloride [containing 84.8% of the (2E,4E) and 4.7% of the (2E,4Z) isomer] as white crystals with melting point 193°–195° C. If desired, this material can be used directly in the subsequent Wittig reaction.

(b) 43.54 g of the phosphonium salt obtained were suspended in 870 ml of toluene under argon. The suspension was heated to reflux for 25 minutes while stirring intensively, then cooled to about 60° C. within 30 minutes and finally cooled to room temperature with a water-bath. The crystals were filtered off under suction, washed three times with 150 ml of toluene each time and once with 300 ml of hexane and then dried at 50° for 1 hour in a water-jet vacuum and at room temperature for 20 hours in a high vacuum. There were thus obtained 38.82 g of (R)-5-(4-hydroxy-2,6,6-trimethyl-1-cyclohexenyl)-3-methyl-2E,4E-pentadienyl-triphenylphosphonium chloride (containing 1.3% of the 2E,4Z isomer) with melting point 196°–198° C.

EXAMPLE 3

A mixture of 22 g of (R)-5-(4-hydroxy-2,6,6-trimethyl-1-cyclohexenyl)-3-methyl-2E,4E-pentadienyl-triphenylphosphonium chloride (prepared according to Example 2), 3.28 g of 2,7-dimethyl-2,4,6-octatrienediol, 80 ml of ethanol and 16 ml of 1,2-butylene oxide was heated to reflux for 20 hours while stirring and gassing with argon, then cooled to −10° C. and stirred at −10° C. for 1 hour. The crystalline product was filtered off under suction, washed three times with 25 ml of cold ethanol each time and dried at 80° C. overnight in a high vacuum. There were thus obtained 10.09 g of red crystals. The mother liquor was concentrated in a rotary evaporator under a water-jet vacuum at 40° C. bath temperature. The residue (16.7 g) was dissolved in 50 ml of ethanol and 5 ml of 1,2-butylene oxide and heated to reflux for 20 hours while stirring and gassing with argon. The mixture was cooled to −10° C. and stirred at −10° C. for 1 hour. The separated crystals were filtered off under suction, washed three times with 10 ml of cold ethanol each time and, together with the first crystallizate, dissolved in 400 ml of chloroform while warming and gassing with argon. After distilling off about 250 ml of chloroform (3R,3'R)-zeaxanthin began to crystallize partially. The remaining chloroform was distilled off within 1.5 hours and was simultaneously replaced by the dropwise addition of 300 ml of ethanol. The suspension was boiled under reflux for a further 1 hour, then cooled to room temperature and stirred at room temperature for a further 1 hour. The crystals were filtered off under suction, washed three times with 25 ml of ethanol each time and dried firstly at 80° C. and then up to constant weight in a high vacuum. There were thus obtained 9.76 g of (3R,3'R)-zeaxanthin as dark red crystals with melting point 201°–202° C.

EXAMPLE 4

(a) 10 g of (R)-4-ethynyl-3,5,5-trimethyl-3-cyclohexen-1-ol were dissolved in 70 ml of absolute tetrahydrofuran under argon. The solution was cooled to −20° C., treated within 5 minutes with 85.9 ml of a 1.56M solution of butyllithium in hexane and stirred at −20° C. for a further 10 minutes. Thereafter, the mixture was treated at −20° C. within 2 minutes with a solution of 5.3 g of lithium bromide in 50 ml of absolute tetrahydrofuran and stirred at −20° C. for a further 15 minutes. The reaction mixture was subsequently treated at −20° C. within 3 minutes with 9.92 ml of methyl vinyl ketone and stirred at −20° C. for a further 1 hour.

(b) Thereafter, the reaction mixture [containing the dilithium salt of (R)-1-(4-hydroxy-2,6,6-trimethyl-1-cyclohexenyl)-3-methyl-4-penten-1-yn-3-ol] was treated at −20° C. within 5 minutes with 34.8 ml of a 3.5M solution of sodium dihydrido-bis(2-methoxyethoxy)aluminate in toluene. The reaction mixture was stirred at 0° C. for a further 2 hours, subsequently treated firstly at −20° C. within 10 minutes with a mixture of 15 ml of ethanol and 20 ml of hexane and then at 0° C. within 10 minutes with 300 ml of 28 percent sodium hydroxide solution and stirred for a further 5 minutes. Thereafter, the reaction mixture was poured into 300 ml of hexane. The aqueous phase was separated and extracted twice with 150 ml of hexane each time. The organic phases were washed twice with 150 ml of 28 percent sodium hydroxide solution each time, dried over sodium sulphate and filtered. The filtrate was evaporated in a rotary evaporator under a water-jet vacuum at 40° C. bath temperature and the residue was dried at room temperature for 2 hours in a high vacuum. There were thus obtained 13.5 g of crude (R)-1-(4-hydroxy-2,6,6-trimethyl-1-cyclohexenyl)-3-methyl-1E,4-pentadien-3-ol as a yellowish oil. Chromatographic purification on silica gel with hexane/diethyl ether gave 9.0 g of product as a colourless oil.

EXAMPLE 5

(a) 10 g of (R)-4-ethynyl-3,5,5-trimethyl-3-cyclohexen-1-ol were dissolved in 30 ml of methylene chloride under argon. The solution was cooled to 0° C. and treated with 12.7 ml of triethylamine. Thereafter, 9.2 ml of trimethylchlorosilane were slowly added dropwise to the reaction mixture at 0° C. The reaction mixture was then left to warm to room temperature and was stirred at room temperature for a further 1.5 hours. The reaction mixture was subsequently poured into 150 ml of saturated sodium bicarbonate solution and extracted three times with 100 ml of methylene chloride each time. The organic phases were washed with 100 ml of semi-saturated sodium bicarbonate solution, dried over sodium sulphate, suction filtered and concentrated. There were thus obtained 14.24 g of (R)-4-ethenyl-3,5,5-trimethyl-1-trimethylsilyloxy-3-cyclohexene as a violet oil.

(b) 7.12 g of (R)-4-ethynyl-3,5,5-trimethyl-1-trimethylsilyloxy-3-cyclohexene were dissolved in 35 ml of tetrahydrofuran under argon. The solution was cooled to −15° C., treated dropwise at −15° C. to −10° C. within 5 minutes with 22.6 ml of a 1.56M solution of butyllithium in hexane and stirred at −17° C. for a further 5 minutes. The mixture was then treated dropwise at −17° C. to −9° C. within 5 minutes with a solution of 2.5 g of lithium bromide in 25 ml of tetrahydrofuran and stirred at −20° C. for a further 10 minutes. The reaction mixture was subsequently treated dropwise at −17° C. within 3 minutes with 3.6 ml of methyl vinyl ketone and stirred at −20° C. for a further 35 minutes.

(c) Thereafter, the reaction mixture [containing the lithium salt of (R)-1-(2,6.6-trimethyl-4-trimethylsilyloxy-1-cyclohexenyl)-3-methyl-4-penten-1-yn-3-ol] was treated dropwise at −20° C. to −13° C. within 5 minutes with 10.2 ml of a 3.5M solution of sodium dihydrido-bis(2-methoxyethoxy)aluminate in toluene and stirred at 0° C. for a further 30 minutes. The reaction mixture was subsequently treated dropwise firstly with a mixture of 6.5 ml of ethanol and 10 ml of hexane and then with 50 ml of 28 percent sodium hydroxide solution. After working-up in an analogous manner to Example 1c there were obtained 10.65 g of crude (R)-1-(2,6,6-trimethyl-4-trimethylsilyloxy-1-cyclohexenyl)-3-methyl-1E,4-pentadien-3-ol as a violet oil; Rf value=0.60 (diisopropyl ether).

(d) 10.65 g of crude (R)-1-(2,6,6-trimethyl-4-trimethylsilyloxy-1-cyclohexenyl)-3-methyl-1E,4-pentadien-3-ol were dissolved in 30 ml of tetrahydrofuran under nitrogen. The solution was treated with 13.8 g of tetrabutylammonium fluoride trihydrate and stirred for a further 20 minutes.. The reaction mixture was subsequently poured into 50 ml of saturated sodium bicarbonate solution and extracted three times with 100 ml of ethyl acetate each time. The organic phases were dried over sodium sulphate, suction filtered and concentrated. Chromatographic purification of the resulting brown oil (9.8 g) with hexane/diethyl ether on silica gel and subsequent drying in a high vacuum gave 6.02 g of (R)-1-(4-hydroxy-2 6 6-trimethyl-1-cyclohexenyl)-3-methyl-1E,4-pentadien-3-ol

EXAMPLE 6

(a) 10 g of (R)-4-ethynyl-3,5,5-trimethyl-3-cyclohexen-1-ol were dissolved in 100 ml of absolute tetrahydrofuran under argon. The solution was treated with 0.2 g of pyridinium p-tosylate, then treated dropwise at 22°–32° C. within 10 minutes with 15 ml of isopropenyl methyl ether and stirred at room temperature for a further 1 hour.

(b) The resulting solution of (R)-4-ethynyl-1-(1-methoxy-1-methylethoxy)-3,5,5-trimethylcyclohexene was treated dropwise at −24° C. to −20° C. within 10 minutes with 50 ml of a 1.56M solution of butyllithium in hexane and stirred at this temperature for a further 15 minutes. The mixture was then treated dropwise at −25° C. to −20° C. within 5 minutes with a solution of 5.28 g of lithium bromide in 100 ml of absolute tetrahydrofuran and subsequently treated dropwise within 10 minutes with a solution of 10 ml of methyl vinyl ketone in 40 ml of absolute tetrahydrofuran. The reaction mixture was stirred at −20° C. for a further 45 minutes, then poured into 200 ml of ice-water, adjusted to pH 3–4 with 20 percent potassium bisulphate solution and extracted three times with 100 ml of diethyl ether each time. The organic phases were washed with 100 ml of saturated sodium chloride solution, dried over sodium sulphate and concentrated. There were thus obtained 25.4 g of a crude product of (R)-1-[4-(1-methoxy-1-methylethoxy)-2,6,6-trimethyl-1-cyclohexenyl]-3-methyl-4-penten-1-yn-3-ol as a yellow oil.

(c) The crude product obtained was dissolved in 150 ml of tetrahydrofuran The solution was treated with 3 ml of water and 0.3 g of pyridinium p-tosylate and stirred at room temperature for 45 minutes. The reaction mixture was subsequently poured into 200 ml of saturated sodium bicarbonate solution and extracted twice with 200 ml of ethyl acetate each time. The organic phases were washed with 100 ml of saturated sodium chloride solution, dried over sodium sulphate and concentrated. The resulting yellow oil (23.4 g) was purified by chromatography on silica gel with hexane/diethyl ether. There were thus obtained 13.65 g (95.6%) of (R)-1-(4-hydroxy-2,6,6-trimethyl-1-cyclohexenyl)-3-methyl-4-penten-1-yn-3-ol as a white crystalline mass.

EXAMPLE 7

(a) 300 g of (4R,6R)-4-hydroxy-2,2,6-trimethylcyclohexanone were dissolved in 154.7 ml of pyridine. The solution was treated dropwise at −3° C. to 0° C. within 10 minutes with 1.2 l of acetic anhydride and then stirred at room temperature for a further 4.25 hours. The reaction mixture was subsequently concentrated on a rotary evaporator at 60° C./16 mbar, whereby there were obtained 394.7 g of crude product as a yellow oil. Distillation of the crude product gave at about 95° C./0.07 mbar 378.4 g (99.4%) of (4R,6R)-4-acetoxy-2,2,6-trimethylcyclohexanone as a colourless oil.

(b) 150 ml of liquid ammonia were placed in a sulphonation flask and 2.8 g of lithium wire were added portionwise within 15 minutes at −45° C. to −40° C. The mixture was stirred at −40° C. for a further 30 minutes 60 l of acetylene (2.4 mol) were then conducted into the mixture within about 45 minutes, whereby a colour change from blue to white took place after conducting in about 16.5 l of acetylene. 150 ml of tetrahydrofuran were subsequently added dropwise to the reaction mixture and ammonia was distilled off from the mixture under a weak stream of acetylene. As soon as the internal temperature had reached 0° C. the introduction of acetylene was discontinued. The reaction mixture was cooled to −10° C., treated dropwise at −15° C. to −10° C. within 15 minutes with a solution of 39.65 g of (4R,6R)-4-acetoxy-2,2,6-trimethylcyclohexanone in 50 ml of absolute tetrahydrofuran and stirred at −15° C. to −10° C. for a further 15 minutes. Thereafter, the reaction mixture was treated at −10° C. to 0° C. within 10 minutes with 100 ml of glacial acetic acid. The mixture was subsequently treated at −10° C. to 0° C. with 100 ml of 2N sulphuric acid and at about 0° C. with 200 ml of water and extracted three times with 200 ml of methylene chloride each time. The organic phases were washed once with 200 ml of semi-saturated sodium chloride solution and twice with 200 ml of semi-saturated sodium bicarbonate solution each time, dried over sodium sulphate and concentrated. There were thus obtained 48.4 g of crude product as an orange oil which, in accordance with gas chromatography, contained (1R,4S,5R)-4-ethynyl-4-hydroxy-3,3,5-trimethylcyclohexyl acetate and 8.8% of (1S,4R,6R)-1-ethynyl-2,2,6-trimethyl-1,4-cyclohexanediol.

The crude product obtained can be directly reacted further according to the method described in Example 10. If desired, before the further reaction, the crude product can be warmed with acetic anhydride in order to convert the diol into (1R,4S,5R)-4-ethynyl-4-hydroxy-3,3,5-trimethylcyclohexyl acetate.

EXAMPLE 8

(a) 156.2 g of (4R,6R)-4-hydroxy-2,2,6-trimethylcyclohexanone were dissolved in 250 ml of absolute tetrahydrofuran under argon. The solution was treated firstly with 0.25 g of pyridinium p-tosylate and then at a temperature of 15°–25° C. within about 20 minutes with 156.5 g of isopropenyl methyl ether. The resulting reaction solution containing (4R,6R)-4-(1-methoxy-1-methylethoxy)-2,2,6-trimethylcyclohexanone was stirred at room temperature for a further 90 minutes and then processed directly.

(b) 750 ml of liquid ammonia were placed in a sulphonation flask and 14 g of lithium wire were added portionwise within 40 minutes at an internal temperature of about −40° C. The mixture was stirred at −40° C. for a further 30 minutes. 150 l of acetylene (6.1 mol) were then conducted into the mixture within 2–3 hours, whereby a colour change from blue to white took place after conducting in about 80 l of acetylene. 750 ml of absolute tetrahydrofuran were subsequently added to the reaction mixture and ammonia was distilled off from the mixture within about 1 hour while continuously introducing acetylene. As soon as the internal temperature had reached about 0° C. the introduction of acetylene was discontinued and the reaction mixture was treated dropwise at 0–2° C. within about 30 minutes with the solution of (4R,6R)-4-(1-methoxy-1-methylethoxy)-2,2,6-trimethylcyclohexanone prepared in paragraph a). The reaction mixture was stirred at 0°–2° C. for a further 30 minutes, then treated at 2°–20° C. within 10 minutes with 400 ml of water and left to stand at room temperature overnight. The reaction mixture was subsequently transferred into a separating funnel with the aid of 700 ml of hexane. The aqueous phase was separated and extracted a further twice with 700 ml of hexane each time. The organic phases were washed with 700 ml of semi-saturated ammonium chloride solution and with 700 ml of semi-saturated sodium chloride solution and then dried over 200 g of sodium sulphate and filtered. The filtrate was evaporated in a rotary evaporator under a water-jet vacuum at 40° C. and the residue was dried at room temperature for 4 hours in a high vacuum. There were thus obtained 260 g of crude (1S,4R,6R)-1-ethynyl-4-(1-methoxy-1-methylethoxy)-2,2,6-trimethyl-1-cyclohexanol as yellow crystals.

(c) 260 g of crude (1S,4R,6R)-1-ethynyl-4-(1-methoxy-1-methylethoxy)-2,2,6-trimethyl-1-cyclohexanol were dissolved in 1300 ml of tetrahydrofuran and 52 ml of water under argon. The solution was treated at room temperature with 2.54 g of pyridinium p-tosylate and stirred for 1 hour. The reaction mixture was subsequently transferred into a separating funnel with the aid of 700 ml of ethyl acetate and then washed with 500 ml of saturated sodium bicarbonate solution and with 500 ml of saturated sodium chloride solution. The aqueous phases were back-extracted twice with ethyl acetate. The organic phases were dried over sodium sulphate and filtered. The filtrate was concentrated in a rotary evaporator under a water-jet vacuum at 40° C. and the residue was dried in a high vacuum for 30 minutes. There were thus obtained 201 g of crude (1S,4R,6R)-1-ethynyl-2,2,6-trimethyl-1,4-cyclohexanediol as colourless crystals; Rf value (hexane/diethyl ether 4:1) 0.25.

EXAMPLE 9

201 g of crude (1S,4R,6R)-1-ethynyl-2,2,6-trimethyl-1,4-cyclohexanediol (prepared according to Example 8) were dissolved in 380 ml of pyridine. The solution was treated at 0° C. within 20 minutes with 500 ml of acetic anhydride and then stirred at room temperature for a further 16 hours. The reaction mixture was subsequently evaporated in a rotary evaporator under a water-jet vacuum. The yellow oil obtained was dissolved in 1 l of methylene chloride and the solution was washed in succession with 500 ml of 2N hydrochloric acid, with 400 ml of cold, saturated sodium chloride solution and with 400 ml of saturated sodium bicarbonate solution. The wash solutions were back-extracted twice with 200 ml of methylene chloride each time. The organic phases were dried over sodium sulphate and filtered The filtrate was concentrated in a rotary evaporator under a water-jet vacuum at 40° C. and the residue was dried at room temperature in a high vacuum for 3 hours. There were thus obtained 246.9 g of crude (1R,4S,5R)-4-ethynyl-4-hydroxy-3,3,5-trimethylcyclohexyl acetate as yellow-brown crystals; Rf value (diisopropyl ether) 0.70.

EXAMPLE 10

121.6 g of crude (1R,4S,5R)-4-ethynyl-4-hydroxy-3,3,5-trimethylcyclohexyl acetate (prepared according to Example 9) were dissolved in 1 l of o-xylene under argon in a sulphonation flask having a water separator. The mixture was treated with 7.9 g of copper(II)sulphate and boiled and stirred intensively for 2 hours under reflux and with the separation of water. The reaction mixture was subsequently cooled to room temperature and the insoluble copper sulphate was filtered off (rinsing with 400 ml of hexane). The filtrate was washed with 400 ml of water and with 400 ml of semisaturated sodium bicarbonate solution The wash solutions were back-extracted twice with 300 ml of hexane each time. The organic phases were dried over sodium sulphate and filtered. The filtrate was concentrated to a volume of about 200–300 ml in a rotary evaporator at 80 Torr and 40°–60° C. bath temperature. Distillation of the residual xylene solution in a high vacuum gave at about 83° C./0.19–0.09 Torr 96.5 g of (R)-4-ethynyl-3,5,5-trimethyl-3-cyclohexen-1-yl acetate (purity 98.1%) as a colourless oil; boiling point 78–82° C./0.14 Torr. The chemical yield amounted to 93% based on (4R,6R)-4-hydroxy-2,2,6-trimethylcyclohexanone.

EXAMPLE 11

183.8 g of (R)-4-ethynyl-3,5,5-trimethyl-3-cyclohexen-1-yl acetate (prepared according to Example 10) were dissolved in 1 l of methanol. The solution was cooled to 0° C. and treated portionwise within 15 minutes with 74.2 g of potassium hydroxide in such a manner that the temperature did not exceed 11° C. The mixture was stirred at 4°–8° C. for a further 15 minutes and then at room temperature for 30 minutes. The reaction mixture was subsequently poured into 2 l of water and 26.5 g of glacial acetic acid. The mixture was extracted three times with 500 ml of methylene chloride each time. The organic phases were washed with 500 ml of saturated sodium chloride solution and with 600 ml of saturated sodium bicarbonate solution, dried over sodium sulphate and filtered. The filtrate was concentrated almost completely in a rotary evaporator under a water-jet vacuum at 30° C. bath temperature. The residual oil was dissolved in 300 ml of pentane and the solution was evaporated completely in a rotary evaporator under a water-jet vacuum at 30° C. bath temperature. The oil obtained was dried at room temperature for 30 minutes in a high vacuum, whereby spontaneous crystallization (strongly exothermic) took place. There were thus obtained 146 g of (R)-4-ethynyl-3,5,5-trimethyl-3-cyclohexen-1-ol (purity 98%, chemical yield 98.8%) as colourless crystals having a pale violet hue; Rf value (diisopropyl ether). 0.40.

We claim:
1. A compound of the formula

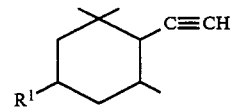

I wherein $R_1$ is selected from the groups consisting of a hydroxy group and an etherified hydroxy group.

2. The compound of claim 1, where $R_1$ is selected from the group consisting of alkoxy, arylalkoxy and a group of the formula,

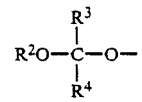

V wherein $R_2$ is alkyl; $R_3$ and $R_4$ are hydrogen or alkyl; or $R_2$ and $R_3$ taken together form tetramethylene.

3. The compound of claim 1, which is (R)-4-ethynyl-3,5,5-trimethyl-3-cyclohexen-1-ol.

4. The compound of claim 2 which is (R)-4-ethynyl-1-(1-methoxy-1-methylethoxy)-3,5,5-trimethyl-3-cyclohexene.

5. A compound of the formula

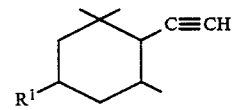

wherein $R_1$ is a trialkylsilyloxy.

6. The compound of claim 5, which is (R)-4-ethynyl-3,5,5-trimethyl-1-trimethlsilyloxy-3-cyclohexene.

* * * * *

UNITED STATES PATENT AND TRADEMARK OFFICE
CERTIFICATE OF CORRECTION

PATENT NO.  : 4,952,716
DATED       : August 28, 1990
INVENTOR(S) : LUKAC, ET AL.

It is certified that error appears in the above-identified patent and that said Letters Patent is hereby corrected as shown below:

In the Abstract, Figure I; in column 1, lines 25-30; in column 14, lines 33-38 and lines 59-63, delete

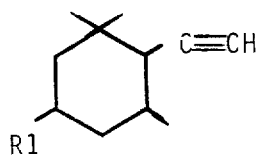

and insert therefor

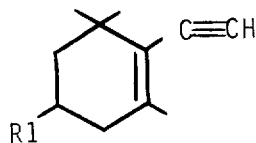

Signed and Sealed this

First Day of September, 1992

Attest:

DOUGLAS B. COMER

Attesting Officer

Acting Commissioner of Patents and Trademarks